United States Patent
Cheung et al.

(10) Patent No.: US 11,702,378 B2
(45) Date of Patent: *Jul. 18, 2023

(54) CATALYTIC HYDROGENATION OF FLUOROOLEFINS, ALPHA-ALUMINA SUPPORTED PALLADIUM COMPOSITIONS AND THEIR USE AS HYDROGENATION CATALYSTS

(71) Applicant: THE CHEMOURS COMPANY FC, LLC, Wilmington, DE (US)

(72) Inventors: Patricia Cheung, Glen Mills, PA (US); Concetta Lamarca, Wilmington, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/479,620

(22) Filed: Sep. 20, 2021

(65) Prior Publication Data

US 2022/0002219 A1 Jan. 6, 2022

Related U.S. Application Data

(60) Continuation of application No. 16/849,059, filed on Apr. 15, 2020, now Pat. No. 11,124,469, which is a continuation of application No. 16/291,548, filed on Mar. 4, 2019, now Pat. No. 10,633,311, which is a continuation of application No. 15/415,960, filed on Jan. 26, 2017, now Pat. No. 10,221,113, which is a division of application No. 14/115,661, filed as application No. PCT/US2012/003822 on May 16, 2012, now Pat. No. 9,598,336.

(60) Provisional application No. 61/486,472, filed on May 16, 2011.

(51) Int. Cl.
| | |
|---|---|
| C07C 17/354 | (2006.01) |
| B01J 21/04 | (2006.01) |
| B01J 23/44 | (2006.01) |
| B01J 35/10 | (2006.01) |
| C07C 21/18 | (2006.01) |
| C07C 19/08 | (2006.01) |

(52) U.S. Cl.
CPC ............ *C07C 17/354* (2013.01); *B01J 21/04* (2013.01); *B01J 23/44* (2013.01); *B01J 35/1009* (2013.01); *C07C 19/08* (2013.01); *C07C 21/18* (2013.01); *C07C 2523/44* (2013.01)

(58) Field of Classification Search
CPC .................................................. C07C 17/354
See application file for complete search history.

(56) References Cited

U.S. PATENT DOCUMENTS

| | | | |
|---|---|---|---|
| 4,533,779 | A | 8/1985 | Boitiaux et al. |
| 4,978,649 | A | 12/1990 | Surovikin et al. |
| 5,136,113 | A | 8/1992 | Rao |
| 5,446,216 | A | 8/1995 | Rao |
| 7,560,602 | B2 | 7/2009 | Van Der Puy et al. |
| 2006/0217579 | A1 | 9/2006 | Bailey |
| 2007/0123741 | A1 | 5/2007 | Van Der Puy et al. |
| 2011/0028770 | A1 | 2/2011 | Wang et al. |
| 2012/0101314 | A1 | 4/2012 | Devic |
| 2012/0101315 | A1 | 4/2012 | Devic |

FOREIGN PATENT DOCUMENTS

| | | |
|---|---|---|
| CN | 101544539 A | 9/2009 |
| EP | 0 703 207 A1 | 3/1996 |
| FR | 2 946 644 A1 | 12/2010 |
| FR | 2 946 645 A1 | 12/2010 |
| JP | 8-165256 A | 6/1996 |
| JP | 8-169851 A | 7/1996 |
| JP | 9-173843 A | 7/1997 |
| JP | 2001-240569 A | 9/2001 |
| JP | 2008-513389 A | 5/2008 |
| JP | 2010-508294 A | 3/2010 |

(Continued)

OTHER PUBLICATIONS

Cotton, F.A. et al., Advanced Inorganic Chemistry, John Wiley & Sons, (1988), Fifth Edition, p. 211-216.

(Continued)

*Primary Examiner* — Medhanit W Bahta

(74) *Attorney, Agent, or Firm* — McNees Wallace & Nurick LLC

(57) ABSTRACT

A hydrogenation process is disclosed. The process involves reacting a fluoroolefin with $H_2$ in a reaction zone in the presence of a palladium catalyst to produce a hydrofluoroalkane product, wherein the palladium catalyst comprises palladium supported on a carrier wherein the palladium concentration is from about 0.001 wt % to about 0.2 wt % based on the total weight of the palladium and the carrier. Also disclosed is a palladium catalyst composition consisting essentially of palladium supported on $\alpha$-$Al_2O_3$ wherein the palladium concentration is from about 0.001 wt % to about 0.2 wt % based on the total weight of the palladium and the $\alpha$-$Al_2O_3$. Also disclosed is a hydrogenation process comprising (a) passing a mixture comprising fluoroolefin and $H_2$ through a bed of palladium catalyst in a reaction zone wherein the palladium catalyst comprises palladium supported on a carrier; and (b) producing a hydrofluoroalkane product; characterized by: the palladium catalyst in the front of the bed having lower palladium concentration than the palladium catalyst in the back of the bed.

14 Claims, No Drawings

(56) References Cited

FOREIGN PATENT DOCUMENTS

| JP | 2011-503200 A | 1/2011 |
|---|---|---|
| JP | 2012-529480 A | 11/2012 |
| JP | 2012-529481 A | 11/2012 |
| WO | 2009093047 A2 | 7/2009 |
| WO | 2009138764 A1 | 11/2009 |
| WO | 2010142877 A1 | 12/2010 |
| WO | 2010142878 A1 | 12/2010 |
| WO | 2011010024 A1 | 1/2011 |
| WO | 2011017138 A2 | 2/2011 |

OTHER PUBLICATIONS

Satterfield, C.N. et al., Heterogeneous Catalysis in Industrial Practice, McGraw-Hill, NY, (1991), Chapter 4, pp. 93-112.
Second Office Action issued in Chinese Application No. 201280023195.0 dated May 11, 2015 (in English and in Chinese).
Official Notice of Rejection dated Aug. 18, 2015, issued in Japanese Patent Application No. 2014-511505 (in Japanese and English).
Chinese Office Action dated Nov. 11, 2015 issued in Application No. 201280023195.0 (in Chinese and English).
Official Notice of Rejection issued in Japanese Patent Application No. 2016-217418 dated Jul. 4, 2017 (in English and Japanese).
Official Notice of Rejection dated Jul. 25, 2017 issued in Japanese Patent Application No. 2014-511505 (in English).
Communication pursuant to Article 94(3) EPC issued in European Patent Application No. 12 725 933.1 dated Jul. 28, 2017.
Office Notice of Rejection issued in Japanese Patent Application No. 2016-217418 dated Dec. 26, 2017.
Examination report under Sections 12 & 13 of the Patents Act issued in Indian Application No. 94899/DELNP/2013 dated Jan. 10, 2018.
WO2010142878A 1, Dec. 16, 2010, pp. 1-2; English translation (Year: 2010).
WO2010142877A 1, Dec. 16, 2010, pp. 1-5; English translation (Year: 2010).
JP2001240569, Sep. 2001, pp. 1-23; English translation (Year: 2001).

CATALYTIC HYDROGENATION OF FLUOROOLEFINS, ALPHA-ALUMINA SUPPORTED PALLADIUM COMPOSITIONS AND THEIR USE AS HYDROGENATION CATALYSTS

CROSS REFERENCE TO RELATED APPLICATIONS

The present application is a continuation of U.S. application Ser. No. 16/849,059, filed on Apr. 15, 2020, which is a continuation of U.S. application Ser. No. 16/291,548, filed on Mar. 4, 2019, now U.S. Pat. No. 10,633,311, which is a continuation of U.S. application Ser. No. 15/415,960, filed on Jan. 26, 2017, now U.S. Pat. No. 10,221,113, which is a divisional application of U.S. Ser. No. 14/115,661, filed on Nov. 5, 2013, now U.S. Pat. No. 9,598,336, which is a '371 of international application having Serial Number PCT/US2012/03822, filed on May 16, 2012, which claims benefit of U.S. Ser. No. 61/486,472, filed on May 16, 2011, the contents of all of which are incorporated by reference.

BACKGROUND

Field of the Disclosure

This disclosure relates in general to the hydrogenation reactions of fluoroolefins with $H_2$ in the presence of a palladium catalyst supported on a carrier, compositions of palladium supported on $\alpha$-$Al_2O_3$ and their use in the fluoroolefin hydrogenation processes.

Description of Related Art

Hydrofluoroalkanes can be employed in a wide range of applications, including their use as refrigerants, solvents, foam expansion agents, cleaning agents, aerosol propellants, dielectrics, fire extinguishants and power cycle working fluids. For example, HFC-236ea ($CF_3CHFCHF_2$) can be used as a heat transfer medium, foam expansion agent, fire extinguishant, et al. Similarly, HFC-245eb ($CF_3CHFCH_2F$) can be used as a heat transfer medium, foam expansion agent, et al. HFC-236ea and HFC-245eb are also intermediates in the production of HFO-1234yf ($CF_3CF=CH_2$) which is a refrigerant with zero ozone depletion potential and low global warming potential.

BRIEF SUMMARY OF THE DISCLOSURE

The present disclosure provides a hydrogenation process. The process comprises reacting a fluoroolefin with $H_2$ in a reaction zone in the presence of a palladium catalyst to produce a hydrofluoroalkane product, wherein said palladium catalyst comprises palladium supported on a carrier wherein the palladium concentration is from about 0.001 wt % to about 0.2 wt % based on the total weight of the palladium and the carrier.

The present disclosure also provides a palladium catalyst composition consisting essentially of palladium supported on $\alpha$-$Al_2O_3$ wherein the palladium concentration is from about 0.001 wt % to about 0.2 wt % based on the total weight of the palladium and the $\alpha$-$Al_2O_3$.

The present disclosure also provides a hydrogenation process comprising reacting a fluoroolefin with $H_2$ in a reaction zone in the presence of a palladium catalyst to produce a hydrofluoroalkane product, characterized by: said palladium catalyst consisting essentially of palladium supported on $\alpha$-$Al_2O_3$ wherein the palladium concentration is from about 0.001 wt % to about 0.2 wt % based on the total weight of the palladium and the $\alpha$-$Al_2O_3$.

The present disclosure also provides a hydrogenation process comprising (a) passing a mixture comprising fluoroolefin and $H_2$ through a bed of palladium catalyst in a reaction zone wherein the palladium catalyst comprises palladium supported on a carrier; and (b) producing a hydrofluoroalkane product; characterized by: the palladium catalyst in the front of the bed having lower palladium concentration than the palladium catalyst in the back of the bed.

DETAILED DESCRIPTION

The hydrogenation reactions of fluoroolefins can be highly exothermic, which can lead to poor temperature control, high levels of undesired byproducts, and safety concerns, et al. Some approaches have been explored to control the heat. For example, Van Der Puy et al. used multiple vapor phase reaction stages as disclosed in U.S. Pat. No. 7,560,602. Also disclosed in U.S. Pat. No. 7,560,602 is an approach of using 1 wt % Pd/C catalysts diluted with inert protruded packing. However, the multiple-reaction-stage design is costly requiring multiple reactors and heat exchangers. The approach of using high Pd loaded (e.g., 1 wt %) catalysts diluted with inert packing could cause highly localized hot spots on the catalyst surface and sintering of highly valuable Pd. Thus, there is a need for cost-effective hydrogenation processes with good heat control.

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

The term "an elevated temperature", as used herein, means a temperature higher than the room temperature.

The term "hydrogenation", as used herein, means a process during which a pair of hydrogen atoms is added to a double bond in an olefin.

The term "fluoroolefin", as used herein, means a molecule containing carbon, fluorine, optionally hydrogen, and at least one carbon-carbon double bond. Of note are fluoroolefins of the formula $C_nH_mF_{2n-m}$ wherein n is an integer from 2 to 8 and m is an integer from 0 to 2n−1. In some embodiments of this invention, n is an integer from 2 to 7. In some embodiments of this invention, the fluoroolefins are terminal fluoroolefins (i.e., the carbon-carbon double bond is at the terminal position) having 3 to 8 carbons. In some embodiments of this invention, the fluoroolefins are terminal fluoroolefins having 3 to 7 carbons. Exemplary fluoroolefins in this disclosure include $CF_3CF=CF_2$ (HFP), $CF_3CF=CHF$ (HFO-1225ye), $CF_3CH=CF_2$, $CF_3CF=CH_2$, $CF_3CH=CHF$, $CF_3CF=CFCF_3$, $CF_3CH=CHCF_3$, $CF_3CH=CFCF_3$, $CF_3CF_2CF=CFCF_3$, $CF_3CF_2CH=CHCF_3$, $(CF_3)_2CFCF=CF_2$, $CF_3CF=CHC_2F_5$, $CF_3CH=CFC_2F_5$, $C_4F_9CH=CH_2$, $CF_3CF_2CF_2CF=CFCF_3$, $CF_3CF_2CF_2CF=CFCF_2CF_3$, $C_2F_5CH=CFCF_2C_2F_5$, $C_2F_5CF=CHCF_2C_2F_5$, and mixtures thereof.

The term "hydrofluoroalkane", as used herein, means a saturated molecule containing hydrogen, carbon, and fluorine.

Disclosed is a hydrogenation process comprising reacting a fluoroolefin with $H_2$ in a reaction zone in the presence of a palladium catalyst to produce a hydrofluoroalkane product, wherein said palladium catalyst comprises palladium supported on a carrier wherein the palladium concentration is from about 0.001 wt % to about 0.2 wt % based on the total weight of the palladium and the carrier. In some embodiments of this invention, the palladium catalyst consists essentially of palladium supported on a carrier wherein the palladium concentration is from about 0.001 wt % to about 0.2 wt % based on the total weight of the palladium and the carrier.

In some embodiments of this invention, the palladium concentration of the palladium catalyst is from about 0.001 wt % to about 0.08 wt % based on the total weight of the palladium and the carrier. In some embodiments of this invention, the palladium concentration of the palladium catalyst is from about 0.001 wt % to about 0.04 wt % based on the total weight of the palladium and the carrier. In some embodiments of this invention, the palladium concentration of the palladium catalyst is from about 0.015 wt % to about 0.025 wt % based on the total weight of the palladium and the carrier.

Also disclosed is a palladium catalyst composition consisting essentially of palladium supported on $\alpha$-$Al_2O_3$ wherein the palladium concentration is from about 0.001 wt % to about 0.2 wt % based on the total weight of the palladium and the $\alpha$-$Al_2O_3$. Also disclosed is the use of such Pd/$\alpha$-$Al_2O_3$ composition as a catalyst in a hydrogenation process. Accordingly, this disclosure also provides a hydrogenation process comprising reacting a fluoroolefin with $H_2$ in a reaction zone in the presence of a palladium catalyst to produce a hydrofluoroalkane product, characterized by: said palladium catalyst consisting essentially of palladium supported on $\alpha$-$Al_2O_3$ wherein the palladium concentration is from about 0.001 wt % to about 0.2 wt % based on the total weight of the palladium and the $\alpha$-$Al_2O_3$.

In some embodiments of this invention, the palladium concentration of the Pd/$\alpha$-$Al_2O_3$ composition is from about 0.001 wt % to about 0.08 wt % based on the total weight of the palladium and the $\alpha$-$Al_2O_3$. In some embodiments of this invention, the palladium concentration of the Pd/$\alpha$-$Al_2O_3$ composition is from about 0.001 wt % to about 0.04 wt % based on the total weight of the palladium and the $\alpha$-$Al_2O_3$. In some embodiments of this invention, the palladium concentration of the Pd/$\alpha$-$Al_2O_3$ composition is from about 0.015 wt % to about 0.025 wt % based on the total weight of the palladium and the $\alpha$-$Al_2O_3$.

In some embodiments of this invention, the fluoroolefin starting material is $C_nH_mF_{2n-m}$ and the hydrofluoroalkane product is $C_nH_{m+2}F_{2n-m}$, wherein n is an integer from 2 to 8 and m is an integer from 0 to 2n−1. In some embodiments of this invention, the fluoroolefin starting material is $CF_3CF=CF_2$ and the hydrofluoroalkane product is $CF_3CHFCHF_2$. In some embodiments of this invention, the fluoroolefin starting material is $CF_3CF=CHF$ and the hydrofluoroalkane product is $CF_3CHFCH_2F$. In some embodiments of this invention, the fluoroolefin starting material is a mixture of two or more fluoroolefins. For example, the fluoroolefin starting material can be a mixture of $CF_3CF=CF_2$ and $CF_3CF=CHF$, and the corresponding hydrofluoroalkane product is a mixture of $CF_3CHFCHF_2$ and $CF_3CHFCH_2F$. For another example, the fluoroolefin starting material can be a mixture of $CF_3CF=CF_2$ and $CF_3CF=CFCF_3$, and the corresponding hydrofluoroalkane product is a mixture of $CF_3CHFCHF_2$ and $CF_3CHFCHFCF_3$. For yet another example, the fluoroolefin starting material can be a mixture of $CF_3CF=CF_2$ and $CF_3CF=CFC_2F_5$, and the corresponding hydrofluoroalkane product is a mixture of $CF_3CHFCHF_2$ and $CF_3CHFCHFC_2F_5$. For yet another example, the fluoroolefin starting material can be a mixture of $CF_3CF=CFC_2F_5$ and $C_2F_5CF=CFCF_2C_2F_5$, and the corresponding hydrofluoroalkane product is a mixture of $CF_3CHFCHFC_2F_5$ and $C_2F_5CHFCHFCF_2C_2F_5$. For yet another example, the fluoroolefin starting material can be a mixture of $CF_3CF=CHC_2F_5$ and $CF_3CH=CFC_2F_5$, and the corresponding hydrofluoroalkane product is a mixture of $CF_3CHFCH_2C_2F_5$ and $CF_3CH_2CHFC_2F_5$. For yet another example, the fluoroolefin starting material can be a mixture of $CF_3CF=CHF$, $CF_3CF=CHC_2F_5$ and $CF_3CH=CFC_2F_5$, and the corresponding hydrofluoroalkane product is a mixture of $CF_3CHFCH_2F$, $CF_3CHFCH_2C_2F_5$ and $CF_3CH_2CHFC_2F_5$. For yet another example, the fluoroolefin starting material can be a mixture of $CF_3CF=CHF$ and $CF_3CH=CFCF_3$, and the corresponding hydrofluoroalkane product is a mixture of $CF_3CHFCH_2F$ and $CF_3CH_2CHFCF_3$.

Some fluoroolefins in this disclosure, e.g., HFO-1225ye, exist as different configurational isomers or stereoisomers. When the specific isomer is not designated, the present disclosure is intended to include all configurational isomers, stereoisomers, or any combination thereof. For instance, HFO-1225ye is meant to represent the E-isomer, Z-isomer, or any combination or mixture of both isomers in any ratio.

The hydrogenation reactions between fluoroolefin and $H_2$ are carried out in the presence of a palladium catalyst. The palladium catalyst in this disclosure is a finely divided zero valent palladium metal supported on a carrier. In some embodiments of this invention, the carrier is selected from the group consisting of $Al_2O_3$, fluorinated $Al_2O_3$, $AlF_3$, carbon, $Cr_2O_3$, $SiO_2$, $TiO_2$, $ZrO_2$ and ZnO.

In some embodiments of this invention, the carrier is carbon. Carbon used in the embodiments of this invention may come from any of the following sources: wood, peat, coal, coconut shells, bones, lignite, petroleum-based residues and sugar. Commercially available carbons which may be used include those sold under the following trademarks: Barneby & Sutcliffe™, Darco™, Nucharm, Columbia JXN™, Columbia LCK™, Calgon™ PCB, Calgon™ BPL, Westvaco™, Norit™, Takeda and Barnaby Cheny NB™.

The carbon also includes three dimensional matrix porous carbonaceous materials. Examples are those described in U.S. Pat. No. 4,978,649. In some embodiments of the invention, carbon includes three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

Carbon includes unwashed and acid-washed carbons. In some embodiments of this invention, suitable carbon carrier may be prepared by treating the carbon with acids such as $HNO_3$, HCl, HF, $H_2SO_4$, $HClO_4$, $CH_3COOH$, and combinations thereof. In some embodiments of this invention, acid is HCl or $HNO_3$. Acid treatment is typically sufficient to provide carbon that contains less than 1000 ppm of ash. Some suitable acid treatments of carbon are described in U.S. Pat. No. 5,136,113. In some embodiments of this invention, a carbon carrier is soaked overnight with gentle stirring in a 1 molar solution of the acid prepared in deionized water. The carbon carrier is then separated and washed at least 10 times with deionized water or until the pH of the washings is about 3. (In some embodiments of this invention, the carbon carrier is then soaked again with gentle stirring in a 1 molar solution of the acid prepared in deionized water for 12 to 24 hours.) The carbon carrier is then finally washed with deionized water until the washings are substantially free of the anion of the acid (e.g., $Cl^-$ or $NO_3^-$), when tested by standard procedures. The carbon carrier is then separated and dried at 120° C. The washed carbon is then soaked in 1 molar HF prepared in deionized water for 48 hours at room temperature with occasional stirring (e.g., in a plastic beaker). The carbon carrier is separated and washed repeatedly with deionized water at 50° C. until the pH of the washings is greater than 4. The carbon carrier is then dried at 150° C. for 60 hours in air followed by calcination at 300° C. for 3 hours in air prior to its use as a carrier.

In some embodiments of this invention, carbon is an activated carbon. In some embodiments of this invention, carbon is an acid washed activated carbon. The carbon can be in the form of powder, granules, or pellets, et al.

In some embodiments of this invention, the carrier is $Al_2O_3$. $Al_2O_3$, also known as alumina, exists in several different phases, e.g., α-, γ-, δ-, η-, θ-, and χ-aluminas. In α-$Al_2O_3$ (corundum), the oxide ions form a hexagonal close-packed structure and the aluminum ions are distributed symmetrically among the octahedral interstices (see F. A. Cotton and G. Wilkinson, *Advanced Inorganic Chemistry, Fifth Edition*, John Wiley & Sons, 1988, page 211). γ-$Al_2O_3$ has a "defect" spinel structure (the structure of spinel with a deficit of cations). Id. In some embodiments of this invention, the carrier is α-$Al_2O_3$. It was surprisingly found through experiments that the hydrogenation processes using α-$Al_2O_3$ as the carrier for the palladium catalysts generate fewer byproducts than other similar hydrogenation processes do when other types of alumina (e.g., γ-$Al_2O_3$) are used as the carriers.

Alumina may be prepared by methods known in the art. For example, the Bayer process is widely used in the industry to produce alumina from bauxite. α-$Al_2O_3$ can be prepared by heating γ-$Al_2O_3$ or any hydrous oxide above 1000° C. Id. γ-$Al_2O_3$ can be prepared by dehydration of hydrous oxides at about 450° C. Id.

The alumina used in this disclosure can be of any suitable shape and dimensions. For example, alumina can be in the form of powder, granules, spheres, or tablets, et al. Typically, alumina used in this disclosure has surface area of from about 1 $m^2/g$ to about 500 $m^2/g$. In some embodiments of this invention, the alumina has surface area of from about 1 $m^2/g$ to about 200 $m^2/g$. In some embodiments of this invention, the alumina has surface area of from about 1 $m^2/g$ to about 50 $m^2/g$. In some embodiments of this invention, the alumina has surface area of from about 1 $m^2/g$ to about 10 $m^2/g$. In some embodiments of this invention, the alumina has surface area of from about 3 $m^2/g$ to about 7 $m^2/g$.

Palladium can be deposited on the carrier using techniques known in the art. For example, the palladium catalysts may be prepared by impregnation methods as generally described by Satterfield on pages 93-112 in *Heterogeneous Catalysis in Industrial Practice*, $2^{nd}$ edition (McGraw-Hill, New York, 1991). Typically, in an impregnation process, a palladium salt is dissolved in a solvent to form a palladium salt solution. Examples of suitable palladium salts for this disclosure include palladium nitrate, palladium chloride, palladium acetate and palladium ammine complexes. Examples of suitable solvents include water and alcohols (e.g., methanol, ethanol, propanol, isopropanol). A carrier is then impregnated with the palladium salt solution. In some embodiments of this invention, a carrier is dipped into an excess amount of the palladium salt solution. In some embodiments of this invention, the incipient wetness technique is used for the impregnation. In an incipient wetness process, a batch of carrier is tumbled and sprayed with an appropriate amount of the palladium salt solution (the amount of the solution is calculated to be just sufficient or slightly less to fill the pores of the carrier). The concentration of the palladium salt solution may be calculated or adjusted so that the finished catalyst has the desired concentration of palladium loaded on the carrier. The incipient wetness technique is also described by Bailey in U.S. Patent Application Publication No. 2006/0217579.

The impregnated carrier is then dried, typically at an elevated temperature. Optionally, the dried impregnated carrier is calcined. The calcination is typically carried out at a temperature of from about 100° C. to about 600° C. In some embodiments of this invention, the calcination is carried out in the presence of an inert gas (e.g., nitrogen, argon) and/or oxygen. The resulting catalyst is then typically treated with a reducing agent prior to use. In some embodiments of this invention, the resulting catalyst is reduced in a flow of hydrogen at an elevated temperature. The hydrogen flow may be diluted with inert gas such as nitrogen, helium, or argon. The reduction temperature is typically from about 100° C. to about 500° C. In some embodiments of this invention, the reduction may be carried out in a liquid phase by hydrazine or formic acid as described by Boitiaux et al. in U.S. Pat. No. 4,533,779.

The hydrogenation process can be carried out in the liquid phase or vapor phase using well-known chemical engineering practice, which includes continuous, semi-continuous or batch operations.

In some embodiments of this invention, the hydrogenation process is carried out in the liquid phase. The liquid phase hydrogenation reaction temperature is typically from about 0° C. to about 200° C. In some embodiments of this invention, the liquid phase hydrogenation reaction temperature is from about 25° C. to about 100° C. The pressure of the liquid phase hydrogenation may vary widely from less than 1 atmosphere to 30 atmospheres or more.

Optionally, the liquid phase hydrogenation process is carried out in the presence of a solvent. The solvent can be polar or non-polar. Suitable polar solvents include water, alcohols, glycol, acetic acid, dimethylformamide (DMF), N-methylpyrrolidone (NMP), triethylamine, and mixtures thereof. In some embodiments of this invention, the polar solvent is methanol, ethanol, or mixtures thereof. Suitable non-polar solvents include inert low dielectric alkanes (e.g., nonane and cyclohexane) and inert low dielectric aromatics (e.g., toluene, benzene and ortho xylene). In some embodiments of this invention, the solvent can also be the expected hydrofluoroalkane product.

In some embodiments of this invention, the hydrogenation process is carried out in the vapor phase. The vapor phase hydrogenation reaction temperature is typically from about room temperature to about 300° C. In some embodiments of this invention, the vapor phase hydrogenation reaction temperature is from about 50° C. to about 200° C.

The vapor phase hydrogenation process can be conducted at superatmospheric, atmospheric, or subatmospheric pressures. In some embodiments of this invention, the vapor phase hydrogenation reaction pressure is from about 10 psig to about 500 psig. In some embodiments of this invention, the vapor phase hydrogenation reaction pressure is from about 50 psig to about 200 psig.

The vapor phase hydrogenation process of this disclosure may be conducted by methods known in the art. In some embodiments of this invention, the fluoroolefin and $H_2$ starting materials, optionally with a diluent, are co-fed to a reactor containing the palladium catalyst. In some embodiments of this invention, the fluoroolefin and $H_2$ starting materials, optionally with a diluent, are passed through the palladium catalyst bed in a reactor.

In some embodiments of this invention, the vapor phase hydrogenation process is conducted without a diluent.

In some embodiments of this invention, the vapor phase hydrogenation process is conducted in the presence of a diluent. In some embodiments of this invention, the diluent is co-fed to the reaction zone with the fluoroolefin and $H_2$ starting materials. In some embodiments of this invention, the molar ratio of the diluent to fluoroolefin starting material co-fed to the reaction zone is from about 100:1 to about 1:1. In some embodiments of this invention, the molar ratio of the diluent to fluoroolefin starting material co-fed to the reaction zone is from about 10:1 to about 1:1. In some embodiments of this invention, the molar ratio of the diluent to fluoroolefin starting material co-fed to the reaction zone is from about 5:1 to about 1:1. The diluent can be an inert gas which does not react under the hydrogenation conditions of this disclosure. In some embodiments of this invention, the diluent is He, Ar, or $N_2$. The diluent can also be the expected hydrofluoroalkane product. For example, when fluoroolefin starting material is HFP, HFC-236ea can be used as the diluent to control the reaction temperature. In some embodiments of this invention, the HFC-236ea diluent is co-fed with HFP and $H_2$ to the reaction zone. For another example, when fluoroolefin starting material is HFO-1225ye, HFC-245eb can be used as the diluent to control the reaction temperature. In some embodiments of this invention, the HFC-245eb diluent is co-fed with HFO-1225ye and $H_2$ to the reaction zone.

In some embodiments of this invention, the diluent is selected from the group consisting of saturated hydrocarbons and saturated hydrofluorocarbons. Suitable saturated hydrocarbons include C1 to C8 alkanes such as methane, ethane, propane et al. Suitable saturated hydrofluorocarbons include C1 to C8 saturated hydrofluorocarbons such as $CHF_3$, $CH_2F_2$, $CHF_2CF_3$, $CHF_2CHF_2$, $CH_2FCF_3$, $CF_3CF_3$, $CF_3CF_2CF_3$, $CF_3CHFCH_2F$, $CF_3CH_2CHF_2$, $CF_3CHFCH_3$, $CF_3CH_2CH_2F$, $CF_3CHFCHF_2$, $CF_3CH_2CF_3$, $CF_3CF_2CH_2F$, $CF_3CH_2CH_2CF_3$, $CF_3CHFCHFC_2F_5$, $C_6F_{14}$, and $C_2F_5CHFCHFC_3F_7$.

The molar ratio of $H_2$ to fluoroolefin fed to the reaction zone in the vapor phase hydrogenation process can be largely varied. Typically, the molar ratio of $H_2$ to fluoroolefin fed to the reaction zone in the vapor phase hydrogenation process is from about 0.1:1 to about 100:1. In some embodiments of this invention, the molar ratio is from about 0.5:1 to about 5:1. In some embodiments of this invention, the molar ratio is from about 0.9:1 to about 3:1.

The effluent from the vapor phase hydrogenation reaction zone is typically a product mixture comprising unreacted starting materials, diluent (if used in the process), the desired hydrofluoroalkane product and some byproducts. The desired hydrofluoroalkane product may be recovered from the product mixture by conventional methods. In some embodiments of this invention, the desired hydrofluoroalkane product may be purified or recovered by distillation. In some embodiments of this invention, the unreacted starting materials, and optionally diluent (if used in the process), are recovered and recycled back to the reaction zone.

Also disclosed is a hydrogenation process comprising (a) passing a gaseous or liquid mixture comprising fluoroolefin and $H_2$ through a bed of palladium catalyst in a reaction zone wherein the palladium catalyst comprises palladium supported on a carrier; and (b) producing a hydrofluoroalkane product; characterized by: the palladium catalyst in the front of the bed having lower palladium concentration than the palladium catalyst in the back of the bed. The front of the bed is the flow entrance to the catalyst bed, and the back of the bed is the flow exit from the catalyst bed. In some embodiments of this invention, the palladium concentration of the catalyst in the front of the bed is from about 0.001 wt % to about 0.2 wt % based on the total weight of the palladium and the carrier, and the palladium concentration of the catalyst in the back of the bed is from about 0.1 wt % to about 1 wt % based on the total weight of the palladium and the carrier. In some embodiments of this invention, the palladium concentration of the catalyst in the front of the bed is from about 0.001 wt % to about 0.08 wt % based on the total weight of the palladium and the carrier, and the palladium concentration of the catalyst in the back of the bed is from about 0.2 wt % to about 0.8 wt % based on the total weight of the palladium and the carrier. In some embodiments of this invention, the palladium concentration of the catalyst in the front of the bed is from about 0.001 wt % to about 0.04 wt % based on the total weight of the palladium and the carrier, and the palladium concentration of the catalyst in the back of the bed is from about 0.3 wt % to about 0.6 wt % based on the total weight of the palladium and the carrier. In some embodiments of this invention, the palladium concentration of the catalyst in the front of the bed is from about 0.015 wt % to about 0.025 wt % based on the total weight of the palladium and the carrier, and the palladium concentration of the catalyst in the back of the bed is from about 0.3 wt % to about 0.6 wt % based on the total weight of the palladium and the carrier.

In some embodiments of this invention, the catalyst bed comprises two or more sections with the same or different lengths wherein each section comprises palladium catalysts having the same palladium concentration. For example, the catalyst bed can comprise a front section and a back section, wherein the front section comprises palladium catalysts with 0.02 wt % palladium concentration and the back section comprises palladium catalysts with 0.5 wt % palladium concentration, and wherein the length of the front section is about 60% of the total bed length and the length of the back section is about 40% of the total bed length. In some embodiments of this invention, the catalyst bed comprises palladium catalysts with continuously increasing palladium concentrations from the front to the back of the catalyst bed.

The reactors, distillation columns, and their associated feed lines, effluent lines, and associated units used in applying the processes of embodiments of this invention may be constructed of materials resistant to corrosion. Typical materials of construction include Teflon™ and glass. Typical materials of construction also include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

EXAMPLES

The concepts described herein will be further described in the following examples, which do not limit the scope of the invention described in the claims.

LEGEND

| | |
|---|---|
| 245eb is $CF_3CHFCH_2F$ | 236ea is $CF_3CHFCHF_2$ |
| HFP is $CF_3CF{=}CF_2$ | 254eb is $CH_3CHFCF_3$ |
| | 1225ye is $CF_3CF{=}CHF$ |

General Procedure for Examples 1-5

The following general procedure is illustrative of the reactor and the thermocouple layout for the temperature measurement. The hydrogenation reaction was carried out by passing a gaseous mixture through a bed of palladium catalyst. 1225ye used herein contained 97-98% Z isomers and 2-3% E isomers. Part of the reactor effluent was sampled on-line for organic product analysis using GC-FID (Gas Chromatograph-Flame Ionization Detector).

A vertically oriented Hastelloy™ reactor (1 inch OD, 0.065 inch wall) jacketed by a recirculating hot oil system was used in all the experiments described below. The reactor was charged with 28.6 cm³ palladium catalysts in the form of ⅛ inch spheres or ⅛ inch×⅛ inch tablets. The palladium catalyst bed in the reactor rose to 3 inches in height and was packed between ⅛ inch Denstone™ $\alpha\text{-}Al_2O_3$ spheres (on top) and ¼ inch Hastelloy™ protruded packing (at the bottom).

The gaseous mixture of starting materials and a diluent was preheated and passed through the reactor entering at the top and exiting at the bottom. A ⅛ inch thermocouple situated along the center of the reactor measured the temperature profile at 8 points: −0.5 inch, 0 inch, 0.5 inch, 1 inch, 1.5 inch, 2 inch, 2.5 inch, and 3 inch. The point of "−0.5 inch" was about 0.5 inch above the catalyst bed; the point of "0 inch" was at about the top of the catalyst bed; and the point of "0.5 inch" was about 0.5 inch below the top of the catalyst bed; and so on.

Example 1

Example 1 demonstrates that hydrogenation of HFP over 0.1 wt % Pd/$\alpha$-$Al_2O_3$ has good control of heat and produces good yields of HFC-236ea with high selectivity.

A gaseous mixture of HFP, $H_2$, and 236ea was fed into the reactor. The HFP flow rate is shown in Table 1. The amount of $H_2$ or 236ea relative to HFP in the gaseous mixture is also shown in Table 1. Table 1 also shows the temperature profile in the reactor and the analytical results of the composition of the effluent from the reactor.

TABLE 1

(Part A)

| Run | Feed Rate HFP (g/h) | Molar Feed Ratios | | Pressure (psig) | Reactor Effluent (mol %) | | |
|---|---|---|---|---|---|---|---|
| | | $H_2$/HFP | 236ea/HFP | | HFP | 236ea | 245eb |
| 1 | 454 | 2.0 | 5.0 | 59 | 4.8 | 95.2 | 0.02 |
| 2 | 454 | 2.0 | 5.0 | 60 | 6.6 | 93.3 | 0.01 |
| 3 | 451 | 2.0 | 6.0 | 60 | 7.6 | 92.4 | 0.01 |
| 4 | 454 | 2.0 | 7.0 | 61 | 7.8 | 92.2 | 0.01 |
| 5 | 455 | 3.0 | 6.0 | 60 | 8.0 | 92.0 | 0.01 |
| 6 | 452 | 4.0 | 5.0 | 60 | 8.0 | 91.9 | 0.01 |
| 7 | 454 | 2.0 | 6.8 | 60 | 8.2 | 91.7 | 0.01 |
| 8 | 452 | 2.0 | 7.0 | 61 | 7.6 | 92.4 | 0.01 |
| 9 | 454 | 2.0 | 7.0 | 61 | 6.7 | 93.2 | 0.01 |
| 10 | 454 | 2.0 | 7.0 | 61 | 6.7 | 93.3 | 0.01 |
| 11 | 457 | 2.0 | 6.9 | 60 | 6.0 | 93.9 | 0.01 |

TABLE 1

(Part B)

| Run | Hot Oil (° C.) | Internal Temperatures (° C.) | | | | | | |
|---|---|---|---|---|---|---|---|---|
| | | −0.5″ | 0″ | 0.5″ | 1″ | 1.5″ | 2″ | 2.5″ | 3″ |
| 1 | 74 | 80 | 79 | 78 | 78 | 81 | 118 | 159 | 166 |
| 2 | 65 | 75 | 73 | 72 | 71 | 72 | 96 | 132 | 143 |
| 3 | 65 | 75 | 74 | 72 | 71 | 72 | 86 | 110 | 119 |
| 4 | 65 | 78 | 76 | 74 | 72 | 73 | 83 | 98 | 106 |
| 5 | 65 | 76 | 74 | 72 | 71 | 72 | 85 | 106 | 116 |
| 6 | 65 | 74 | 72 | 71 | 70 | 71 | 88 | 117 | 130 |
| 7 | 65 | 76 | 75 | 73 | 72 | 72 | 81 | 95 | 102 |
| 8 | 74 | 81 | 80 | 79 | 78 | 79 | 91 | 107 | 114 |
| 9 | 84 | 85 | 85 | 85 | 85 | 87 | 101 | 121 | 130 |
| 10 | 94 | 91 | 92 | 92 | 93 | 95 | 110 | 130 | 138 |
| 11 | 104 | 95 | 97 | 98 | 99 | 102 | 121 | 144 | 152 |

Example 2

Example 2 demonstrates that hydrogenation of HFP over 0.04 wt % Pd/$\alpha$-$Al_2O_3$ has good control of heat and produces good yields of HFC-236ea with high selectivity.

A gaseous mixture of HFP, $H_2$, and 236ea was fed into the reactor. The HFP flow rate is shown in Table 2. The amount of H$_2$ or 236ea relative to HFP in the gaseous mixture is also shown in Table 2. Table 2 also shows the temperature profile in the reactor and the analytical results of the composition of the effluent from the reactor.

TABLE 2

(Part A)

| Run | Feed Rate HFP (g/h) | Molar Feed Ratios H$_2$/HFP | 236ea/HFP | Pressure (psig) | Reactor Effluent (mol %) HFP | 236ea | 245eb |
|---|---|---|---|---|---|---|---|
| 1 | 91 | 2.0 | 10.0 | 125 | 1.4 | 98.5 | 0.03 |
| 2 | 138 | 2.0 | 6.6 | 125 | 1.5 | 98.5 | 0.03 |
| 3 | 228 | 2.0 | 3.9 | 125 | 2.2 | 97.7 | 0.04 |
| 4 | 226 | 1.2 | 3.0 | 125 | 4.4 | 95.6 | 0.03 |
| 5 | 226 | 1.2 | 5.0 | 100 | 6.5 | 93.5 | 0.01 |
| 6 | 227 | 2.0 | 5.0 | 100 | 5.6 | 94.4 | 0.01 |
| 7 | 226 | 3.0 | 5.1 | 100 | 5.3 | 94.7 | 0.01 |
| 8 | 226 | 3.0 | 4.9 | 100 | 4.8 | 95.1 | 0.01 |
| 9 | 227 | 3.0 | 5.0 | 100 | 4.3 | 95.7 | 0.01 |
| 10 | 226 | 2.0 | 5.0 | 100 | 7.5 | 92.5 | 0.01 |

TABLE 2

(Part B)

| Run | Hot Oil (° C.) | Internal Temperatures (° C.) −0.5″ | 0″ | 0.5″ | 1″ | 1.5″ | 2″ | 2.5″ | 3″ |
|---|---|---|---|---|---|---|---|---|---|
| 1 | 84 | 86 | 97 | 116 | 130 | 134 | 134 | 131 | 127 |
| 2 | 85 | 87 | 103 | 132 | 151 | 155 | 154 | 149 | 143 |
| 3 | 84 | 88 | 110 | 154 | 180 | 185 | 182 | 174 | 166 |
| 4 | 84 | 89 | 121 | 172 | 195 | 196 | 189 | 179 | 168 |
| 5 | 84 | 86 | 95 | 113 | 129 | 138 | 143 | 145 | 143 |
| 6 | 84 | 86 | 95 | 115 | 132 | 142 | 147 | 149 | 147 |
| 7 | 85 | 86 | 95 | 115 | 132 | 143 | 148 | 150 | 148 |
| 8 | 94 | 95 | 105 | 127 | 144 | 155 | 159 | 161 | 159 |
| 9 | 104 | 104 | 116 | 140 | 159 | 168 | 172 | 172 | 169 |
| 10 | 114 | 114 | 124 | 144 | 158 | 165 | 167 | 167 | 165 |

Example 3

Example 3 demonstrates that hydrogenation of HFP over 0.02 wt % Pd/α-Al$_2$O$_3$ has good control of heat and produces good yields of HFC-236ea with high selectivity.

A gaseous mixture of HFP, H$_2$, and 236ea was fed into the reactor. The HFP flow rate is shown in Table 3. The amount of H$_2$ or 236ea relative to HFP in the gaseous mixture is also shown in Table 3. Table 3 also shows the temperature profile in the reactor and the analytical results of the composition of the effluent from the reactor.

TABLE 3

(Part A)

| Run | Feed Rate HFP (g/h) | Molar Feed Ratios H$_2$/HFP | 236ea/HFP | Pressure (psig) | Reactor Effluent (mol %) HFP | 236ea | 245eb |
|---|---|---|---|---|---|---|---|
| 1 | 91 | 2.0 | 9.9 | 100 | 6.2% | 93.7% | 0.02% |
| 2 | 137 | 2.0 | 6.7 | 99 | 8.6% | 91.4% | 0.02% |
| 3 | 227 | 3.0 | 4.0 | 100 | 12.9% | 87.0% | 0.02% |
| 4 | 228 | 3.0 | 3.0 | 102 | 11.9% | 88.0% | 0.03% |
| 5 | 135 | 2.0 | 6.8 | 100 | 9.1% | 90.9% | 0.01% |
| 6 | 226 | 2.0 | 4.0 | 100 | 13.3% | 86.7% | 0.01% |
| 7 | 226 | 3.0 | 3.1 | 101 | 14.3% | 85.6% | 0.02% |
| 8 | 227 | 3.0 | 3.0 | 125 | 8.6% | 91.3% | 0.05% |
| 9 | 226 | 3.0 | 3.0 | 125 | 11.3% | 88.7% | 0.01% |
| 10 | 227 | 1.2 | 2.9 | 125 | 13.7% | 86.3% | 0.01% |
| 11 | 226 | 1.2 | 3.0 | 125 | 9.3% | 90.7% | 0.02% |
| 12 | 228 | 1.2 | 3.0 | 125 | 14.9% | 85.1% | 0.01% |
| 13 | 227 | 3.0 | 3.0 | 125 | 11.9% | 88.1% | 0.01% |
| 14 | 226 | 1.2 | 2.0 | 125 | 10.8% | 89.1% | 0.02% |
| 15 | 229 | 0.5 | 2.0 | 125 | 24.2% | 75.7% | 0.00% |
| 16 | 228 | 1.2 | 2.2 | 125 | 10.9% | 89.1% | 0.02% |
| 17 | 227 | 3.0 | 3.0 | 125 | 14.0% | 85.9% | 0.01% |

TABLE 3

(Part B)

| Run | Hot Oil (° C.) | Internal Temperatures (° C.) −0.5″ | 0″ | 0.5″ | 1″ | 1.5″ | 2″ | 2.5″ | 3″ |
|---|---|---|---|---|---|---|---|---|---|
| 1 |  | 84 | 85 | 88 | 91 | 93 | 96 | 98 | 100 |
| 2 | 84 | 84 | 85 | 89 | 93 | 96 | 101 | 105 | 108 |
| 3 | 84 | 85 | 86 | 90 | 96 | 101 | 110 | 118 | 124 |
| 4 | 84 | 85 | 86 | 92 | 101 | 111 | 127 | 142 | 152 |
| 5 | 85 | 84 | 85 | 88 | 91 | 94 | 99 | 103 | 106 |
| 6 | 84 | 84 | 85 | 89 | 94 | 99 | 107 | 115 | 121 |
| 7 | 84 | 85 | 86 | 90 | 97 | 104 | 117 | 130 | 138 |
| 8 | 85 | 94 | 98 | 108 | 123 | 140 | 160 | 173 | 177 |
| 9 | 94 | 85 | 87 | 94 | 105 | 117 | 135 | 149 | 158 |
| 10 | 85 | 94 | 97 | 105 | 117 | 129 | 143 | 153 | 159 |
| 11 | 94 | 114 | 120 | 137 | 162 | 180 | 193 | 197 | 194 |
| 12 | 114 | 84 | 87 | 93 | 102 | 111 | 124 | 133 | 139 |
| 13 | 84 | 85 | 87 | 93 | 104 | 114 | 130 | 142 | 151 |
| 14 | 84 | 85 | 91 | 107 | 136 | 164 | 188 | 194 | 189 |
| 15 | 85 | 85 | 87 | 94 | 104 | 113 | 123 | 127 | 128 |
| 16 | 84 | 85 | 92 | 111 | 142 | 167 | 186 | 189 | 181 |
| 17 | 84 | 85 | 87 | 93 | 101 | 109 | 120 | 129 | 136 |

Example 4

Example 4 demonstrates that hydrogenation of 1225ye over 0.1 wt % Pd/α-Al$_2$O$_3$ has good control of heat and produces good yields of HFC-245eb with high selectivity.

A gaseous mixture of 1225ye, H$_2$, and 245eb was fed into the reactor. The 1225ye flow rate is shown in Table 4. The amount of H$_2$ or 245eb relative to 1225ye in the gaseous mixture is also shown in Table 4.

Table 4 also shows the temperature profile in the reactor and the analytical results of the composition of the effluent from the reactor.

TABLE 4

(Part A)

| Run | Feed Rate 1225ye (g/h) | Molar Feed Ratios H$_2$/1225ye | 245eb | Pressure (psig) | Reactor Effluent (mol %) 1225ye | 254eb | 245eb |
|---|---|---|---|---|---|---|---|
| 1 | 91 | 2.0 | 9.9 | 75 | 1.9 | 0.17 | 97.9 |
| 2 | 135 | 2.0 | 6.6 | 75 | 2.5 | 0.16 | 97.4 |
| 3 | 226 | 2.0 | 4.0 | 75 | 2.7 | 0.18 | 97.0 |

TABLE 4-continued

(Part A)

| Run | Feed Rate 1225ye (g/h) | Molar Feed Ratios H₂/1225ye | Molar Feed Ratios 245eb | Pressure (psig) | Reactor Effluent (mol %) 1225ye | Reactor Effluent (mol %) 254eb | Reactor Effluent (mol %) 245eb |
|---|---|---|---|---|---|---|---|
| 4 | 339 | 2.0 | 2.7 | 75 | 3.9 | 0.22 | 95.8 |
| 5 | 226 | 1.5 | 5.9 | 75 | 4.4 | 0.09 | 95.4 |
| 6 | 226 | 2.0 | 4.0 | 76 | 3.0 | 0.12 | 96.8 |
| 7 | 227 | 2.0 | 4.0 | 60 | 3.7 | 0.10 | 96.2 |
| 8 | 227 | 2.0 | 4.0 | 60 | 3.6 | 0.09 | 96.3 |
| 9 | 227 | 4.0 | 2.1 | 60 | 2.4 | 0.16 | 97.4 |
| 10 | 227 | 3.0 | 3.0 | 60 | 2.7 | 0.12 | 97.2 |
| 11 | 227 | 1.5 | 6.0 | 60 | 5.0 | 0.09 | 94.9 |
| 12 | 271 | 1.2 | 4.9 | 60 | 6.5 | 0.09 | 93.4 |
| 13 | 343 | 1.2 | 3.7 | 60 | 7.8 | 0.10 | 92.1 |
| 14 | 452 | 1.2 | 2.6 | 60 | 8.4 | 0.12 | 91.5 |
| 15 | 226 | 2.0 | 4.0 | 60 | 4.0 | 0.08 | 95.9 |
| 16 | 92 | 2.0 | 9.8 | 60 | 2.8 | 0.06 | 97.1 |
| 17 | 228 | 2.0 | 4.0 | 60 | 4.3 | 0.10 | 95.6 |
| 18 | 227 | 0.5 | 4.0 | 60 | 11.2 | 0.09 | 88.7 |
| 19 | 225 | 2.0 | 4.0 | 60 | 4.4 | 0.09 | 95.5 |

TABLE 4

(Part B)

| Run | Hot Oil (° C.) | Internal Temperatures (° C.) −0.5" | 0" | 0.5" | 1" | 1.5" | 2" | 2.5" | 3" |
|---|---|---|---|---|---|---|---|---|---|
| 1 |  | 85 | 91 | 108 | 121 | 126 | 127 | 125 | 122 |
| 2 | 85 | 86 | 94 | 118 | 138 | 145 | 146 | 143 | 138 |
| 3 | 85 | 87 | 100 | 139 | 172 | 182 | 181 | 175 | 167 |
| 4 | 84 | 87 | 102 | 156 | 202 | 215 | 215 | 208 | 197 |
| 5 | 84 | 82 | 86 | 102 | 122 | 134 | 140 | 144 | 143 |
| 6 | 85 | 87 | 97 | 132 | 166 | 178 | 180 | 175 | 167 |
| 7 | 85 | 87 | 97 | 130 | 163 | 176 | 178 | 174 | 166 |
| 8 | 85 | 77 | 86 | 118 | 152 | 167 | 169 | 166 | 158 |
| 9 | 75 | 77 | 95 | 155 | 195 | 196 | 184 | 167 | 152 |
| 10 | 75 | 77 | 90 | 135 | 175 | 185 | 181 | 172 | 160 |
| 11 | 75 | 77 | 80 | 93 | 111 | 123 | 130 | 134 | 132 |
| 12 | 75 | 77 | 81 | 97 | 119 | 133 | 140 | 144 | 142 |
| 13 | 75 | 77 | 82 | 102 | 132 | 150 | 159 | 163 | 160 |
| 14 | 75 | 77 | 86 | 119 | 166 | 189 | 198 | 199 | 193 |
| 15 | 75 | 77 | 84 | 112 | 147 | 164 | 168 | 166 | 159 |
| 16 | 75 | 76 | 79 | 88 | 99 | 106 | 109 | 111 | 109 |
| 17 | 75 | 77 | 83 | 106 | 140 | 159 | 166 | 166 | 160 |
| 18 | 75 | 78 | 83 | 99 | 117 | 124 | 124 | 122 | 117 |
| 19 | 75 | 77 | 84 | 109 | 144 | 162 | 167 | 166 | 159 |

Example 5

Example 5 demonstrates that hydrogenation of 1225ye over 0.02 wt % Pd/α-Al₂O₃ has good control of heat and produces good yields of HFC-245eb with high selectivity.

A gaseous mixture of 1225ye, H₂, and 245eb was fed into the reactor. The 1225ye flow rate is shown in Table 5. The amount of H₂ or 245eb relative to 1225ye in the gaseous mixture is also shown in Table 5. Table 5 also shows the temperature profile in the reactor and the analytical results of the composition of the effluent from the reactor.

TABLE 5

(Part A)

| Run | Feed Rate 1225ye (g/h) | Molar Feed Ratios H₂/1225ye | Molar Feed Ratios 245eb/1225ye | Pressure (psig) | Reactor Effluent (mol %) 1225ye | Reactor Effluent (mol %) 254eb | Reactor Effluent (mol %) 245eb |
|---|---|---|---|---|---|---|---|
| 1 | 92 | 1.9 | 9.8 | 75 | 5.0% | 0.10% | 94.9% |
| 2 | 138 | 2.0 | 6.6 | 75 | 6.9% | 0.08% | 93.0% |
| 3 | 228 | 2.0 | 3.9 | 75 | 10.4% | 0.09% | 89.5% |
| 4 | 227 | 3.0 | 2.9 | 74 | 10.7% | 0.12% | 89.1% |
| 5 | 228 | 3.0 | 2.9 | 75 | 10.7% | 0.11% | 89.2% |
| 6 | 226 | 3.0 | 3.0 | 75 | 9.9% | 0.09% | 89.9% |
| 7 | 228 | 3.0 | 3.0 | 75 | 9.7% | 0.09% | 90.2% |
| 8 | 227 | 3.0 | 3.0 | 75 | 9.4% | 0.08% | 90.5% |
| 9 | 226 | 3.0 | 3.0 | 75 | 11.8% | 0.06% | 88.2% |
| 10 | 228 | 3.0 | 3.0 | 77 | 9.9% | 0.07% | 90.0% |
| 11 | 226 | 4.0 | 2.0 | 75 | 9.2% | 0.10% | 90.6% |
| 12 | 114 | 2.5 | 7.6 | 75 | 4.7% | 0.11% | 95.2% |
| 13 | 222 | 1.3 | 2.9 | 75 | 11.2% | 0.02% | 88.7% |
| 14 | 114 | 1.2 | 5.6 | 75 | 9.1% | 0.03% | 90.8% |
| 15 | 225 | 1.2 | 3.0 | 75 | 12.7% | 0.03% | 87.3% |
| 16 | 226 | 2.0 | 3.0 | 75 | 10.8% | 0.04% | 89.1% |
| 17 | 226 | 4.0 | 3.0 | 75 | 9.9% | 0.04% | 90.0% |
| 18 | 227 | 5.9 | 3.0 | 75 | 9.9% | 0.05% | 90.0% |
| 19 | 225 | 3.0 | 3.0 | 75 | 12.5% | 0.04% | 87.4% |

TABLE 5

(Part B)

| Run | Hot Oil (° C.) | Internal Temperatures (° C.) −0.5" | 0" | 0.5" | 1" | 1.5" | 2" | 2.5" | 3" |
|---|---|---|---|---|---|---|---|---|---|
| 1 | 85 | 85 | 87 | 91 | 97 | 100 | 104 | 103 | 103 |
| 2 | 84 | 85 | 87 | 93 | 101 | 106 | 112 | 111 | 110 |
| 3 | 84 | 85 | 88 | 97 | 111 | 119 | 128 | 127 | 125 |
| 4 | 84 | 85 | 90 | 104 | 124 | 135 | 142 | 139 | 140 |
| 5 | 94 | 95 | 100 | 117 | 137 | 147 | 151 | 148 | 151 |
| 6 | 104 | 104 | 110 | 128 | 148 | 157 | 160 | 157 | 160 |
| 7 | 114 | 114 | 120 | 142 | 163 | 171 | 172 | 168 | 173 |
| 8 | 124 | 123 | 131 | 154 | 176 | 183 | 183 | 179 | 185 |
| 9 | 85 | 85 | 90 | 105 | 123 | 131 | 137 | 135 | 136 |
| 10 | 104 | 104 | 110 | 130 | 152 | 160 | 164 | 161 | 164 |
| 11 | 104 | 105 | 114 | 146 | 176 | 181 | 175 | 168 | 180 |
| 12 | 104 | 107 | 127 | 161 | 170 | 162 | 144 | 137 | 154 |
| 13 | 104 | 103 | 105 | 111 | 118 | 122 | 127 | 127 | 125 |
| 14 | 104 | 104 | 109 | 118 | 128 | 131 | 132 | 130 | 132 |
| 15 | 104 | 104 | 109 | 124 | 141 | 147 | 151 | 149 | 150 |
| 16 | 104 | 104 | 110 | 129 | 151 | 159 | 164 | 161 | 164 |
| 17 | 104 | 104 | 109 | 127 | 149 | 158 | 164 | 161 | 163 |
| 18 | 104 | 104 | 109 | 125 | 147 | 157 | 162 | 159 | 162 |
| 19 | 84 | 85 | 88 | 99 | 116 | 125 | 136 | 135 | 132 |

General Procedure for Examples 6-7

The following general procedure is illustrative of the reactor and the thermocouple layout for the temperature measurement. The hydrogenation reaction was carried out by passing a gaseous mixture through a bed of palladium catalyst. Part of the reactor effluent was sampled on-line for organic product analysis using GC-FID (Gas Chromatograph-Flame Ionization Detector).

An Inconel™ reactor (⅝ inch OD, 0.034 inch wall) jacketed by an aluminum sleeve was used in all the experiments described below. The sleeve was heated by a 5 inch long heater band furnace. The reactor was charged with 5 cm³ palladium catalysts in the form of ⅛ inch spheres or ⅛ inch×⅛ inch tablets.

The gaseous mixture of HFP, H₂, and N₂ was pre-heated to 50° C. and passed through the reactor in the direction of from the top of the catalyst bed to the bottom. The furnace temperature was controlled by a thermocouple inside the aluminum sleeve. A 1/16 inch thermocouple situated along the center of the reactor measured the temperature profile at about the top of the catalyst bed (0" point) and about 1 inch below the top (1" point).

Example 6

Example 6 demonstrates that hydrogenation of HFP over 0.3 wt % Pd/γ-$Al_2O_3$ generates considerable amount of 245eb byproduct.

A gaseous mixture of HFP, $H_2$, and $N_2$ was fed into the reactor. The HFP flow rate is shown in Table 6. The amount of $H_2$ and $N_2$ relative to HFP in the gaseous mixture is also shown in Table 6. Table 6 also shows the temperature profile in the reactor and the analytical results of the composition of the effluent from the reactor.

TABLE 6

| Run | Feed Rate HFP (sccm) | Molar Feed Ratios | | Furnace (° C.) | Internal Temperatures (° C.) | | Reactor Effluent (mol %) | | |
|---|---|---|---|---|---|---|---|---|---|
| | | $H_2$/HFP | $N_2$/HFP | | 0" | 1" | HFP | 236ea | 245eb |
| 1 | 10 | 1 | 10 | 49 | 80 | 52 | 11.9 | 85.7 | 2.0 |
| 2 | 10 | 5 | 10 | 50 | 75 | 51 | 0.1 | 99.0 | 0.9 |
| 3 | 10 | 1 | 30 | 51 | 84 | 59 | 13.1 | 83.4 | 2.8 |
| 4 | 5 | 1 | 60 | 51 | 84 | 59 | 10.9 | 85.5 | 2.9 |
| 5 | 10 | 1 | 30 | 70 | 101 | 76 | 13.7 | 82.5 | 3.0 |
| 6 | 4.9 | 2 | 61 | 69 | 86 | 74 | 1.9 | 95.9 | 1.9 |
| 7 | 4.8 | 1 | 61 | 70 | 87 | 75 | 9.5 | 87.4 | 2.5 |

Example 7

Example 7 demonstrates that hydrogenation of HFP over 0.3 wt % Pd/α-$Al_2O_3$ does not generate 245eb byproduct.

A gaseous mixture of HFP, $H_2$, and $N_2$ was fed into the reactor. The HFP flow rate is shown in Table 7. The amount of $H_2$ and $N_2$ relative to HFP in the gaseous mixture is also shown in Table 7. Table 7 also shows the temperature profile in the reactor and the analytical results of the composition of the effluent from the reactor.

TABLE 7

| Run | Feed Rate HFP (sccm) | Molar Feed Ratios | | Furnace (° C.) | Internal Temperatures (° C.) | | Reactor Effluent (mol %) | | |
|---|---|---|---|---|---|---|---|---|---|
| | | $H_2$/HFP | $N_2$/HFP | | 0" | 1" | HFP | 236ea | 245eb |
| 1 | 10 | 1 | 30 | 49 | 56 | 55 | 49.27 | 50.47 | 0.00 |
| 2 | 10 | 5 | 30 | 48 | 62 | 55 | 8.67 | 91.13 | 0.00 |
| 3 | 10 | 2.5 | 30 | 51 | 64 | 59 | 19.20 | 80.54 | 0.00 |
| 4 | 20 | 2.5 | 15 | 47 | 77 | 62 | 14.91 | 84.83 | 0.00 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

What is claimed is:

1. A process comprising flowing a composition comprising at least one fluoroolefin across a bed of a palladium catalyst supported on a carrier comprising α-$Al_2O_3$, the bed having a front and a back, the composition flowing from the front of the bed to the back of the bed, wherein a concentration of the palladium catalyst in the bed spatially increases continuously from a first concentration of palladium catalyst in the front of the bed to a second concentration of palladium catalyst in the back of the bed, the second concentration of palladium catalyst being greater than the first concentration of palladium catalyst, wherein the at least one fluoroolefin has the formula $C_nH_mF_{2n-m}$, wherein n is an integer from 2 to 8 and m is an integer from 0 to 2n−1.

2. The process of claim 1, wherein the composition further comprises hydrogen ($H_2$) and the process is a hydrogenation process.

3. The process of claim 2, wherein n=3, m=2, and the at least one fluoroolefin is defined by the formula $C_3H_2F_4$.

4. The process of claim 2, wherein n=3 and m=0.

5. The process of claim 2, wherein n=3 and m=1.

6. The process of claim 3, wherein the at least one fluoroolefin is selected from the group consisting of $CF_3CH\!=\!CHF$ and $CF_3CF\!=\!CH_2$.

7. The process of claim 1, wherein the at least one fluoroolefin is selected from the group consisting of $CF_3CF\!=\!CF_2$ and $CF_3CF\!=\!CHF$.

8. The process of claim 2, wherein the hydrogenation process is carried out in one of a liquid phase or a vapor phase.

9. The process of claim 8, wherein the hydrogenation process is carried out at a temperature of between about 0° C. and about 200° C.

10. The process of claim 8, wherein the hydrogenation process is carried out at a temperature of between about room temperature and about 300° C.

11. The process of claim 2, wherein the hydrogenation process is conducted with $H_2$ and fluoroolefin fed at a molar ratio of about 0.1:1 to about 100:1.

12. The process of claim 2, wherein the first palladium concentration is from about 0.001 wt % to about 0.08 wt % based on the total weight of the palladium and the carrier in the front of the bed, and the second palladium concentration is from about 0.2 wt % to about 0.8 wt % based on the total weight of the palladium and the carrier in the back of the bed.

13. The process of claim 2, wherein the hydrogenation process is conducted with $H_2$ and fluoroolefin fed at a molar ratio of about 0.5:1 to about 5:1.

14. The process of claim 2, wherein the hydrogenation process is conducted with $H_2$ and fluoroolefin fed at a molar ratio of about 0.9:1 to about 3:1.

\* \* \* \* \*